United States Patent [19]

Axen

[11] 4,197,257

[45] Apr. 8, 1980

[54] 6-KETO PROSTAGLANDIN DERIVATIVES

[75] Inventor: Udo F. Axen, Plainwell, Mich.

[73] Assignee: The Upjohn Company, Kalamazoo, Mich.

[21] Appl. No.: 959,401

[22] Filed: Nov. 9, 1978

Related U.S. Application Data

[60] Division of Ser. No. 819,857, Jul. 28, 1977, which is a continuation-in-part of Ser. No. 725,548, Sep. 22, 1976, abandoned, which is a continuation-in-part of Ser. No. 716,972, Aug. 23, 1976, abandoned, which is a continuation-in-part of Ser. No. 655,110, Feb. 4, 1976, abandoned.

[51] Int. Cl.² .................. A61K 31/16; C07C 103/19; C07C 103/737
[52] U.S. Cl. .................. 260/557 R; 260/559 R; 260/559 B; 260/563 R; 260/570.5 CA; 260/586 R; 548/253; 424/269; 424/299; 424/320; 424/324; 424/325; 424/330; 424/331; 424/324; 560/121; 562/503
[58] Field of Search .......... 260/557 R, 559 R, 559 B; 562/503

[56] References Cited

U.S. PATENT DOCUMENTS 3,927,197  12/1975  Monkhouse .................. 260/557 R X

OTHER PUBLICATIONS

Pace–Asciak, JACS, 98, 2348 (1976).

*Primary Examiner*—Thomas A. Waltz
*Attorney, Agent, or Firm*—Morris L. Nielsen; Robert A. Armitage

[57] ABSTRACT

Prostaglandin ($PG_1$) derivatives having (1) a 6-keto feature, for example

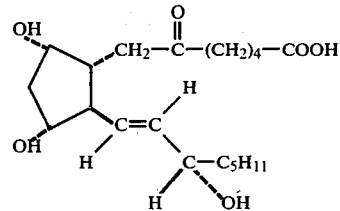

and amides thereof or (2) a 9-deoxy-6,9-epoxy feature together with a 5-halo or 6-hydroxy feature, for example

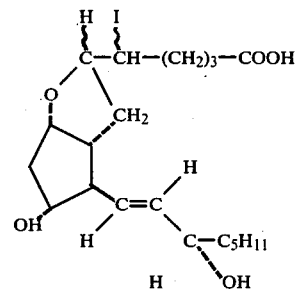

or

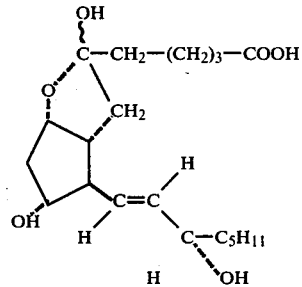

said derivatives having pharmacological activity. Processes for preparing them and the appropriate intermediates are disclosed.

17 Claims, No Drawings

6-KETO PROSTAGLANDIN DERIVATIVES

CROSS REFERENCE TO RELATED APPLICATIONS

This is a division, of application Ser. No. 819,857, filed July 28, 1977.

This application is a continuation-in-part of copending application Ser. No. 725,548 filed Sept. 22, 1976, now abandoned which was a continuation-in-part of then copending application Ser. No. 716,972 filed Aug. 23, 1976, since abandoned, which was a continuation-in-part of then copending application Ser. No. 655,110, filed Feb. 4, 1976, and since abandoned.

The essential material for this application is incorporated by reference under the provisions of M.P.E.P. 608.01(p), from pending and commonly owned U.S. application Ser. No. 819,857, now U.S. Pat. No. 4,158,667.

BACKGROUND OF THE INVENTION

This invention relates to prostaglandin derivatives and to a process for preparing them.

The prostaglandins and analogs are well-known organic compounds derived from prostanoic acid which has the following structure and atom numbering:

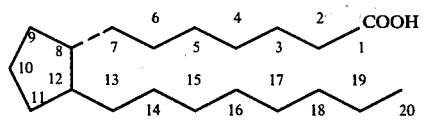

As drawn hereinafter the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background, see for example Bergstrom et al., Pharmacol. Rev. 20, 1 (1968) and Pace-Asciak et al., Biochem. 10, 3657 (1971). Subsequent to this invention there appeared a publication on 6-keto-prostaglandin F$_{1\alpha}$ by Pace-Asciak, J. Am. Chem. Soc. 98, 2348 (1976) and a publication on "PGX" (alternatively 6,9α-oxido-9α,15α-dihydroxyprosta-(Z)5, (E)13-dienoic acid) by E. J. Corey et al., J. Am. Chem. Soc. 99, 2006 (1977).

SUMMARY OF THE INVENTION

It is the purpose of this invention to provide novel products having pharmacological activity. It is a further purpose to provide a process for preparing these products and their intermediates.

Accordingly, there is provided a compound of the formula:

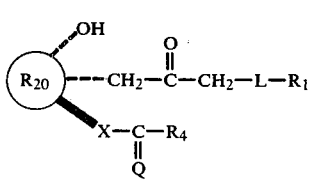

or a mixture comprising that compound and the enantiomer thereof wherein R$_{20}$ is

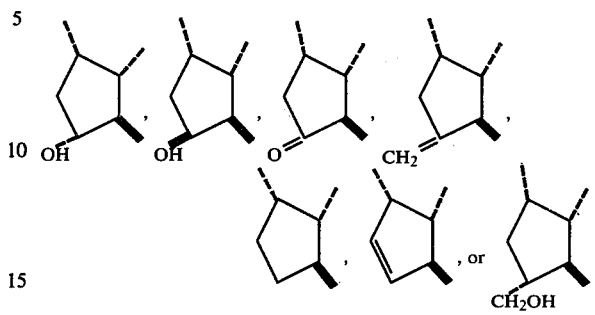

wherein

L is (1) —(CH$_2$)$_d$—C(R$_2$)$_2$—

(2) —CH$_2$—O—CH$_2$—Y— or (3) —CH$_2$CH=CH— wherein d is zero for 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—, wherein Q is

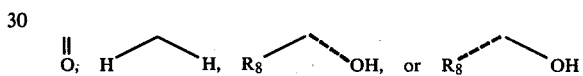

wherein

R$_8$ is hydrogen or alkyl of one to 4 carbon atoms, inclusive, wherein

R$_1$ is (1) —COOR$_3$ (2) —CH$_2$OH (3) —CH$_2$N(R$_9$)(R$_{18}$)

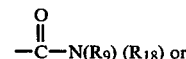

(4)

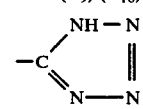

(5)

wherein

R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

(g)

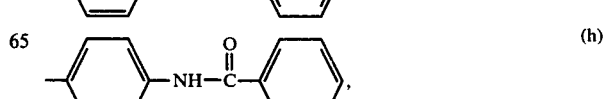

(h)

-continued

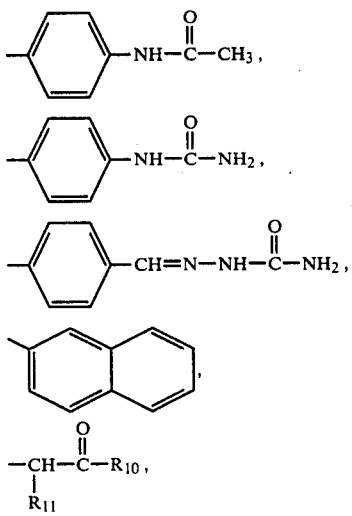

wherein
R₁₀ is phenyl, p-bromophenyl, p-biphenylyl, p-nitrophenyl, p-benzamidophenyl, or 2-naphthyl, and wherein R₁₁ is hydrogen or benzoyl, or (n) a pharmacologically acceptable cation, wherein R₉ is hydrogen, methyl, or ethyl, and R₁₈ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein
R₄ is

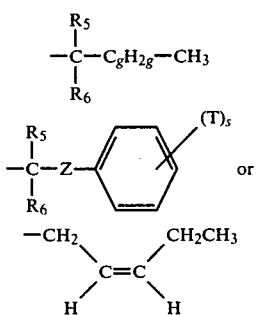

wherein
$C_gH_{2g}$ is alkylene of one to 9 carbon atoms, inclusive, with one to 5 carbon atoms, inclusive, in the chain between $-CR_5R_6-$ and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between CR₅R₆— and the phenyl ring; wherein T is alkyl of one to 4 carbon atoms, inclusive, fluoro, chloro, trifluoromethyl, or —OR₇— wherein R₇ is alkyl of one to 4 carbon atoms, inclusive, and s is zero, one, 2 or 3, with the proviso that not more than two T's are other than alkyl and when s is 2 or 3 the T's are either the same or different; and wherein
X is
(1) trans—CH=CH—
(2) cis—CH=CH—
(3) —C≡C— or
(4) —CH₂CH₂—;
including the lower alkanoates thereof.

In formula I as used herein, attachment to R₂₀ and R₂₁ corresponds to bonds to the cyclopentane ring at the C-8, C-9, and C-12 positions following prostaglandin nomenclature, thus:

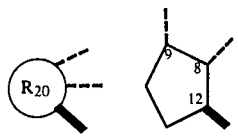

Within the scope of the prostaglandin derivatives described herein there are represented
(a) PGF_α compounds when R₂₀ is

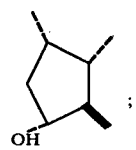

(b) 11β-PGF_α compounds when R₂₀ is

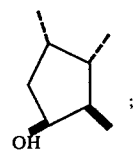

(c) 11-Deoxy-11-keto-PGF_α compounds when R₂₀ is

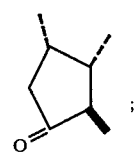

(d) 11-Deoxy-11-methylene-PGF_α compounds when R₂₀ is

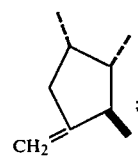

(e) 11-Deoxy-PGF_α compounds when R₂₀ is

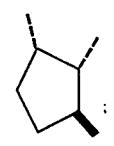

(f) 11-Deoxy-10,11-Didehydro-PGF$_\alpha$ compounds when 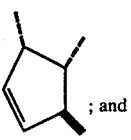 is

 ; and (g) 11-Deoxy-11-hydroxymethyl-PGF$_\alpha$ compounds when 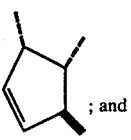 is

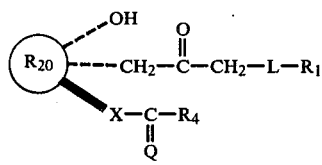

It is claimed:
1. A compound of the formula

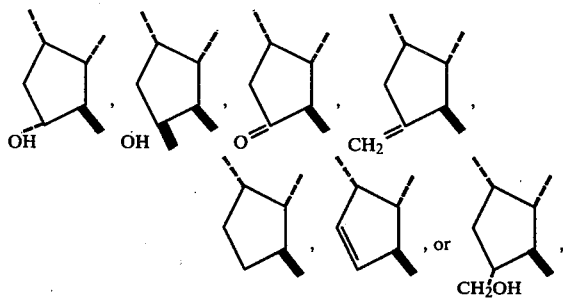

or a mixture comprising that compound and the enantiomer thereof wherein 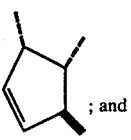 is

wherein
L is
(1) —(CH$_2$)$_d$—C(R$_2$)$_2$—
(2) —CH$_2$—O—CH$_2$—Y— or
(3) —CH$_2$CH=CH— wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein
Q is

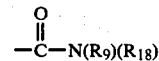

wherein
R$_8$ is hydrogen or alkyl of one to 4 carbon atoms, inclusive,
wherein
R$_1$ is

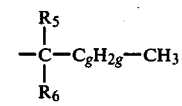

wherein
R$_9$ is hydrogen, methyl, or ethyl, and R$_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;
wherein
R$_4$ is

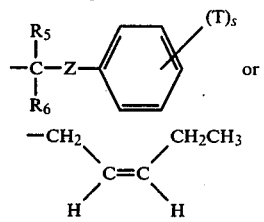

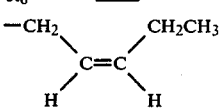

wherein
C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the phenyl ring; wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different; and
wherein
X is
(1) trans—CH=CH—
(2) cis—CH=CH—
(3) —C≡C— or
(4) —CH$_2$CH$_2$—.

2. A compound according to claim 1 wherein 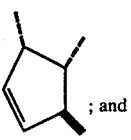 is

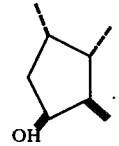

3. A compound according to claim 1 wherein 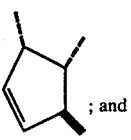 is

4. A compound according to claim 1 wherein $R_{20}$ is

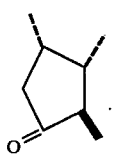

5. A compound according to claim 1 wherein $R_{20}$ is

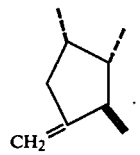

6. A compound according to claim 1 wherein $R_{20}$ is

7. A compound according to claim 1 wherein $R_{20}$ is

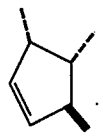

8. A compound according to claim 1 wherein $R_{20}$ is

wherein
L is —$(CH_2)_n$—, n being 3, 4, or 5, wherein Q is

wherein
$R_8$ is limited to hydrogen, methyl, or ethyl, and
wherein
$R_4$ is n-pentyl, 1,1-dimethylpentyl, 1,1-difluoropentyl,

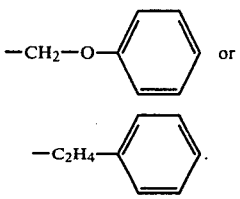

9. A compound according to claim 8 wherein $R_1$ is $$-\overset{O}{\underset{\|}{C}}-N(R_9)(R_{18})$$

wherein
$R_9$ and $R_{18}$ are as defined in claim 1.

10. 6-Keto-PGF$_{1\alpha}$, amide, a compound according to claim 9.

11. 6-Keto-PGF$_{1\alpha}$, methylamide, a compound according to claim 9.

12. 6-Keto-PGF$_{1\alpha}$, benzylamide, a compound according to claim 9.

13. 6-Keto-PGF$_{1\alpha}$, anilide, a compound according to claim 9.

14. A compound according to claim 11 wherein X is —C≡C—.

15. A compound according to claim 8 wherein X is —$CH_2CH_2$—.

16. A compound according to claim 8 wherein X is trans—CH=CH—.

17. 6-Keto-PGF$_{1\alpha}$, n-butylamide, a compound according to claim 16.

* * * * *

UNITED STATES PATENT OFFICE
CERTIFICATE OF CORRECTION

Patent No. 4,197,257  Dated  8 April 1980

Inventor(s)  Udo F. Axen

It is certified that error appears in the above-identified patent and that said Letters Patent are hereby corrected as shown below:

In the abstract, in that portion of the second and third formulas reading

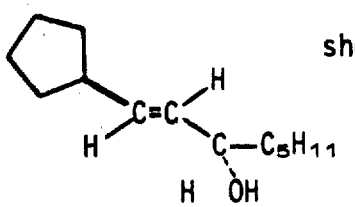   should read   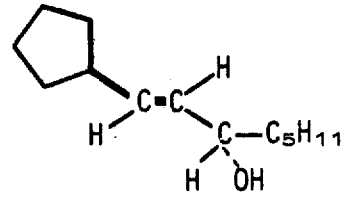

Column 8, line 47, "according to claim 11" should read -- according to claim 8 --.

Signed and Sealed this

Twenty-fourth Day of March 1981

[SEAL]

Attest:

RENE D. TEGTMEYER

Attesting Officer    Acting Commissioner of Patents and Trademark